(12) United States Patent  
Watanabe et al.

(10) Patent No.: US 11,806,421 B2
(45) Date of Patent: Nov. 7, 2023

(54) POROUS-CELLULOSE PARTICLES AND PRODUCTION METHOD THEREOF, AND COSMETIC

(71) Applicant: JGC CATALYSTS AND CHEMICALS LTD., Kanagawa (JP)

(72) Inventors: Satoshi Watanabe, Kitakyushu (JP); Naoyuki Enomoto, Kitakyushu (JP); Ikuko Shimazaki, Kitakyushu (JP)

(73) Assignee: JGC CATALYSTS AND CHEMICALS LTD., Kanagawa (JP)

( * ) Notice: Subject to any disclaimer, the term of this patent is extended or adjusted under 35 U.S.C. 154(b) by 277 days.

(21) Appl. No.: 17/255,284

(22) PCT Filed: Jun. 28, 2019

(86) PCT No.: PCT/JP2019/025758
§ 371 (c)(1),
(2) Date: Dec. 22, 2020

(87) PCT Pub. No.: WO2020/004604
PCT Pub. Date: Jan. 2, 2020

(65) Prior Publication Data
US 2021/0259942 A1  Aug. 26, 2021

(30) Foreign Application Priority Data
Jun. 29, 2018 (JP) .................. 2018-124651

(51) Int. Cl.
*A61K 8/73* (2006.01)
*A61K 8/06* (2006.01)
(Continued)

(52) U.S. Cl.
CPC ............... *A61K 8/731* (2013.01); *A61K 8/06* (2013.01); *A61K 2800/10* (2013.01);
(Continued)

(58) Field of Classification Search
None
See application file for complete search history.

(56) References Cited

U.S. PATENT DOCUMENTS 6,225,461 B1    5/2001  Akimoto et al.
2009/0022791 A1* 1/2009  Obae .................. A61K 9/2059
                                                424/464

(Continued)

FOREIGN PATENT DOCUMENTS

JP    H02-84401 A    3/1990
JP    H06-254373 A   9/1994
(Continued)

OTHER PUBLICATIONS

Wada, et al., Polymorphism of Cellulose I Family: Reinvestigation of Cellulose IV, Biomacromolecules 5 (2004) pp. 1385-1391. (Year: 2004).*

(Continued)

*Primary Examiner* — Dominic Lazaro
(74) *Attorney, Agent, or Firm* — Pearne & Gordon, LLP

(57) ABSTRACT

The porous-cellulose particles according to the present invention are constituted by gathered crystalline celluloses having a type I crystal form including a glucose molecule as a constitutional unit. That is, porous-cellulose particles having high sphericity have been achieved from a natural raw material. The porous-cellulose particles have an average particle diameter of 0.5 to less than 50 μm, a specific surface area of 50 to 1000 m²/g, and a sphericity of 0.85 or more. Cosmetic products containing such porous-cellulose particles have excellent texture properties.

10 Claims, 1 Drawing Sheet

(51) Int. Cl.
*B82Y 5/00* (2011.01)
*B82Y 40/00* (2011.01)

(52) U.S. Cl.
CPC .............. *A61K 2800/21* (2013.01); *B82Y 5/00* (2013.01); *B82Y 40/00* (2013.01)

(56) References Cited

U.S. PATENT DOCUMENTS

| | | | |
|---|---|---|---|
| 2010/0087552 A1 | 4/2010 | Shiomi et al. | |
| 2013/0172538 A1 | 7/2013 | Hirano et al. | |
| 2015/0297820 A1* | 10/2015 | Kawai | C08B 16/00 106/122 |
| 2016/0244483 A1 | 8/2016 | Okubo et al. | |
| 2016/0355662 A1 | 12/2016 | Tokuoka et al. | |
| 2018/0280256 A1 | 10/2018 | Watanabe et al. | |

FOREIGN PATENT DOCUMENTS

| | | |
|---|---|---|
| JP | H10-195103 A | 7/1998 |
| JP | H11-181147 A | 7/1999 |
| JP | 2013-133355 A | 7/2013 |
| JP | 2015-187255 A | 10/2015 |
| JP | 2016-153449 A | 8/2016 |
| JP | 2017-088873 A | 5/2017 |
| JP | 2018-172578 A | 11/2018 |
| WO | 2006-115198 A1 | 11/2006 |
| WO | 2008-084854 A1 | 7/2008 |
| WO | 2012-033223 A1 | 3/2012 |
| WO | 2014-038686 A1 | 3/2014 |
| WO | 2015-046473 A1 | 4/2015 |

OTHER PUBLICATIONS

International Search Report dated Sep. 24, 2019 Issued in Patent Application No. PCT/JP2019/025758.

* cited by examiner

POROUS-CELLULOSE PARTICLES AND PRODUCTION METHOD THEREOF, AND COSMETIC

TECHNICAL FIELD

The present invention relates to porous-cellulose particles constituted by gathered celluloses having good biodegradability, and particularly relates to porous-cellulose particles having high sphericity and cosmetic products containing the porous-cellulose particles.

BACKGROUND ART

Today, synthetic polymers (plastics) derived from petroleum are being used in various industries, and support the convenience in our lives. Many of the synthetic polymers have been developed to secure long-term stability. Therefore, synthetic polymers are not degraded in natural environment, causing various environmental problems. One of such problems is that plastic products flowing out to aqueous environment accumulate for an extended period, and have significantly harmful effects on the ecosystems of oceans and lakes. Also, fine plastics having a length of from not more than 5 mm to nano levels, which are called micro-plastics, are recently considered as another serious problem. Examples of the micro-plastics include fine particles contained in cosmetic products and the like, small chunks of unprocessed plastic resin, and micro-pieces resulting from the fragmentation of large products floating in the sea.

Recent cosmetic products include plastic particles (e.g., polyethylene particles) having a size in orders of several hundreds of micrometers, so that texture property of the cosmetic products improves. Plastic particles, which have a small true specific gravity, are difficult to remove at sewage treatment plants, resulting in outflow into rivers, oceans, ponds, and the like. Since plastic particles are likely to adsorb chemicals such as pesticides, human bodies possibly have adverse effects due to biological concentration. This issue is also pointed out in the United Nations Environment Programme and the like. Various countries and industry associations are considering framing regulations against this problem.

Also, natural cosmetic products and organic cosmetic products are of increasing interest. A guideline on marking of natural and organic indices of cosmetic products (ISO16128) has been established. According to this guideline, raw materials in products are categorized into, for example, a natural raw material, a naturally derived raw material, and a non-natural raw material. Based on a contained amount of each raw material, an index is calculated. In the future, the index will be marked on a product in accordance with this guideline. Therefore, a naturally derived raw material, and furthermore, a natural raw material will be demanded.

Under such circumstances, biodegradable plastics are attracting an attention. The biodegradable plastics are decomposed into water and carbon dioxide by, for example, microorganisms in a natural environment. So, the biodegradable plastics are incorporated in a natural carbon cycle. Especially, cellulose particles being a plant-derived natural raw material do not float on water even when discharged into the environment and also have good biodegradability. Therefore, there is little concern about the possibility that cellulose particles may cause environmental problems. For example, it is known that spherical regenerated cellulose particles of 9 to 400 nm are obtained by neutralizing with an acid a cuprammonium solution in which cellulose is dissolved (for example, see PATENT LITERATURE 1). It is also known that spherical regenerated cellulose particles are obtained by spraying a cellulose solution to form droplets in a gas phase and bringing the droplets into contact with a coagulation liquid (for example, see PATENT LITERATURE 2). In these methods, cellulose particles are prepared with celluloses having a type II crystal form obtained through a process of performing intentional chemical modification. Such regenerated cellulose particles are categorized as a naturally derived raw material according to the above-described guideline. On the other hand, powdery cellulose particles having a strength and collapsibility suitable for a scrub agent, which are prepared with celluloses obtained through a process of performing no intentional chemical modification, are also known (for example, see PATENT LITERATURE 3). Also, it is known that porous-cellulose particles having a type I crystalline form are prepared by granulating and drying celluloses dispersed in an organic solvent by a spray dry method (for example, see PATENT LITERATURE 4).

CITATION LIST

Patent Literatures

PATENT LITERATURE 1: JP-T-2008-84854
PATENT LITERATURE 2: JP-A-2013-133355
PATENT LITERATURE 3: JP-A-2017-88873
PATENT LITERATURE 4: JP-A-2-84401

SUMMARY OF THE INVENTION

Problems to be Solved by the Invention

Cellulose particles used as an alternative to plastic beads in cosmetic products have the following two requirements.
(1) Being formed with I-type crystalline celluloses obtained through a process of performing no intentional chemical modification, so as to be regarded as a natural raw material.
(2) Having high sphericity and good fluidity and improving texture properties of cosmetic products.

The regenerated cellulose particles described in PATENT LITERATURES 1 and 2 were not regarded as a natural raw material in accordance with the above-described guideline. Also, the cellulose particles described in PATENT LITERATURE 3, which have a sphericity of 0.1 to 0.7, were unable to provide good texture properties to cosmetic products. Like in PATENT LITERATURE 4, cellulose particles can be obtained by a spray dry method. However, particles obtained by a spray dry method did not have sufficient sphericity, because the drying speed is fast. Therefore, even if the particles were formulated in cosmetic products, uniform rolling properties were unable to be obtained.

Therefore, an object of the present invention is to achieve porous-cellulose particles having both high sphericity and good fluidity with celluloses having a type I crystal form obtained through a process of performing no intentional chemical modification. With cosmetic products containing such porous-cellulose particles, there is little concern about the possibility that an environmental problem may be caused, and furthermore, texture properties similar to those of known plastic beads can be obtained.

Solution to Problems

The porous-cellulose particles according to the present invention are particles constituted by gathered crystalline celluloses. The porous-cellulose particles have an average particle diameter $d_1$ of 0.5 to less than 50 μm, a specific surface area of 25 to 1000 m²/g, and a sphericity of 0.85 or more. Here, the crystalline celluloses have a type I crystal form including a glucose molecule as a constitutional unit.

Also, the pore volume PV is set in a range of 0.2 to 5.0 ml/g. Furthermore, the average pore diameter PD is set in a range of 2 to 200 nm. Also, crystalline celluloses having an average particle diameter $d_3$ of 1 nm to 1 μm are used. Also, as porous-cellulose particles, hollow particles having a cavity inside a shell are used.

Furthermore, when an aqueous dispersion liquid of the porous-cellulose particles is dispersed by an ultrasonic disperser for 60 minutes, a ratio ($d_2/d_1$) between an average particle diameter $d_2$ after dispersion and an average particle diameter $d_1$ before dispersion is in a range of 0.95 to 1.05.

The production method of porous-cellulose particles according to the present invention includes: an emulsification step of mixing a dispersion liquid of crystalline celluloses having a type I crystal form, a surfactant, and a nonaqueous solvent to prepare an emulsified liquid containing emulsified droplets, a dehydration step of dehydrating the emulsified droplets, and a step of separating the nonaqueous solvent dispersion body obtained in the dehydration step into solid and liquid to obtain porous-cellulose particles as solid matter.

Also, the emulsified liquid obtained in the emulsification step may be cooled to a range of 0 to −50° C. to obtain a frozen emulsified liquid in which water in the emulsified droplets is frozen.

Any of the above-described porous-cellulose particles can be formulated together with cosmetic ingredients to prepare cosmetic products.

DESCRIPTION OF EMBODIMENTS

Figure 1:
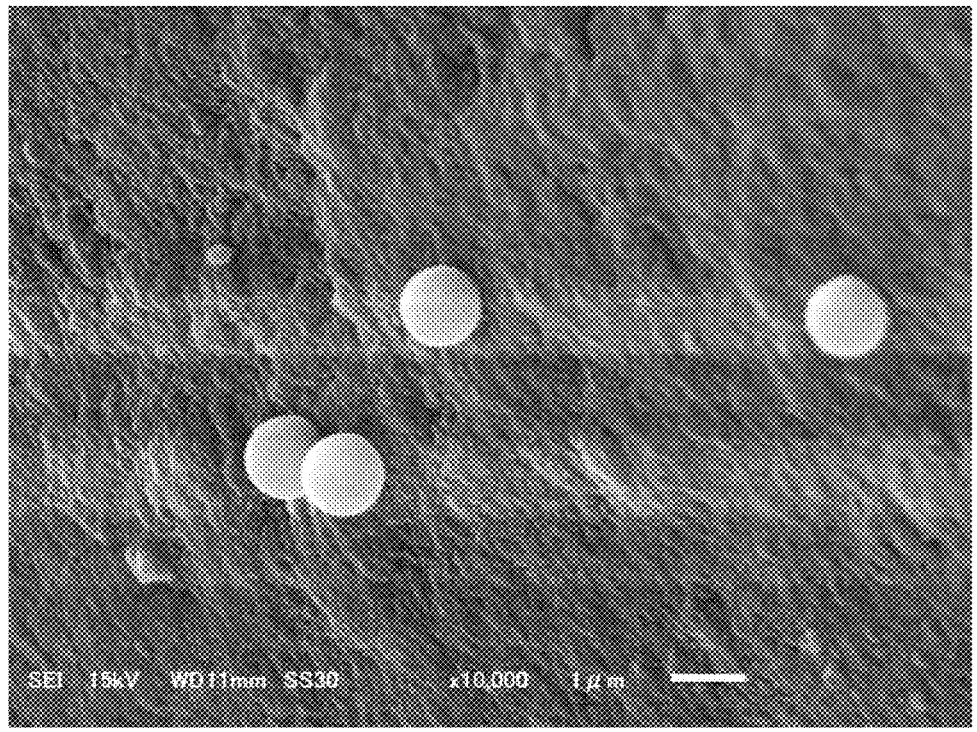
FIG. 1 is a SEM photograph illustrating appearances of porous-cellulose particles according to Example 1.

The porous-cellulose particles according to the present invention are constituted by gathered crystalline celluloses having "a type I crystal form including a glucose molecule as a constitutional unit" (hereafter, termed "I-type crystalline celluloses"). The porous-cellulose particles have an average particle diameter ($d_1$) equal to or greater than 0.5 μm and smaller than 50 μm, a sphericity equal to or greater than 0.85, a specific surface area within the range from 25 m²/g to 1000 m²/g. The average particle diameter of the porous-cellulose particles gives an influence on the texture characteristics of the cosmetic products. If the average particle diameter is smaller than 0.5 μm, the texture characteristics such as rolling feel, persistence of rolling feel, and uniform spreadability would be deteriorated significantly. If the average particle diameter is greater than 50 μm, a powder of the particles would feel coarse, less soft and less moist. It is more preferable that the average particle diameter ($d_1$) range from 1 μm to 20 μm, and most preferable that the mean particle diameter ($d_1$) range from 1 μm to 10 μm. The average particle diameter ($d_1$) can be determined by a laser diffraction method.

When the specific surface area is less than 25 m²/g, a biodegradation speed when flowing out into aqueous environments is not sufficient. On the other hand, when the specific surface area exceeds 1000 m²/g, particles become brittle and sometimes collapse when applied onto the skin. The specific surface area is particularly preferably 50 to 500 m²/g.

Also, cosmetic products containing particles having a sphericity of less than 0.85 do not exhibit good rolling properties. The sphericity is particularly preferably 0.90 or more. As described herein, the sphericity was calculated from a photograph of a scanning electron microscope by an image analysis method.

The coefficient of particle variance (CV) of the porous-cellulose particles is preferably 50% or less. When the coefficient of particle variance exceeds 50%, uniform rolling properties may be impaired. The coefficient of particle variance is preferably 40% or less and particularly preferably 30% or less. It is noted that the coefficient of particle variance is suitably as small as possible. However, it is industrially difficult to obtain particles having a narrow distribution. When roughly 3% or more, a problem is not particularly raised in terms of production.

Here, the content of I-type crystalline celluloses in the porous particles is desirably 50% or more. Celluloses having other crystal forms, such as types 11 to IV, may be contained. The content of I-type crystalline celluloses is preferably 75% or more and particularly preferably 90% or more. The larger the content, the higher the natural index according to the above-described guideline. It is noted that the crystal form of celluloses can be identified by infrared spectroscopy. For a type I crystal form, a strong absorption is observed at 3365 to 3370 cm$^{-1}$. Furthermore, the identification also can be performed based on a difference in chemical shift by solid-state 13C NMR spectroscopy or a diffraction angle by X-ray diffraction. Also, the crystal form may be any one of Iα and Iβ structures or a mixture thereof.

Furthermore, the porous-cellulose particles preferably have a pore volume (PV) of 0.2 to 5.0 ml/g and an average pore diameter (PD) of 2 to 2000 nm. For particles having a pore volume of less than 0.2 ml/g, the elasticity is low, and soft texture properties are unlikely to be obtained. On the other hand, for particles having a pore volume of mom than 5.0 ml/g, the strength is brittle, and the particles are likely to collapse when applied onto the skin. The pore volume is more preferably 0.2 to 2.0 ml/g. Also, when the average pore diameter is less than 2 nm, texture properties are not significantly affected, but biodegradability decreases. On the other hand, when more than 200 nm, the strength of particles becomes brittle.

When the porous-cellulose particles collapse during the manufacturing process of a cosmetic product, the resultant cosmetic product may not have a function as initially expected. To address this problem, it is preferable that the average particle diameter of the particles exhibit a rate of change remaining substantially the same before and after application of ultrasound to a dispersion liquid of the particles. Specifically, the porous-cellulose particles are dispersed in distilled water to obtain dispersion liquid. The dispersion liquid is to an ultrasonic disperser to be dispersed for 60 minutes. The ratio ($d_2/d_1$) between the average particle diameter ($d_2$) after the dispersion test and the average particle diameter ($d_1$) before the dispersion test is preferably between 0.95 and 1.05. The ratio ($d_2/d_1$) smaller than 0.95 means that the particles have a low strength and may collapse due to a mechanical load applied in the manufacturing process of the cosmetic product, and that desired texture improvement may not be achieved. The ratio ($d_2/d_1$) greater than 1.05 means that the particles easy to swell in water. As a result, the viscosity of the manufactured cosmetic product tends to increase, making it impossible to ensure quality stability. This may also change the texture characteristics. It is particularly preferable that the ratio ($d_2/d_1$) is between 0.97 and 1.03.

Also, as the porous-cellulose particle, a particle having a hollow structure in which a cavity is formed inside a shell can be adopted. The hollow particle is lighter than a solid particle having an identical diameter. Therefore, when the component amount (% by weight) is identical, the number of hollow particles is larger than the number of solid particles. Here, the shell may be porous to allow nitrogen gas to pass through. Furthermore, a ratio (T/OD) between a thickness T of the shell and an outer diameter OD of the porous-cellulose particle is preferably in the range of 0.02 to 0.45. When the shell thickness ratio (T/OD) exceeds 0.45, the particle comes to be substantially equivalent to a particle that does not have a hollow structure. On the other hand, when the shell thickness ratio is less than 0.02, the particle comes to easily break. The shell thickness ratio (T/OD) is particularly preferably in the range of 0.04 to 0.30.

It is preferable that I-type crystalline cellulose, which forms the porous-cellulose particles, have an average particle diameter ($d_3$) ranging from 1 nm to 1 μm. The porous-cellulose particles produced using the I-type crystalline cellulose having such a micro average particle diameter can exhibit a suitable biodegradability. It is particularly preferable that the average particle diameter of the crystalline cellulose be within the range from 0.1 μm to 0.5 μm. Apart from the particles described above, cellulose nanofibers having a thickness ranging from 1 nm to 500 nm and a length of 1 μm or more (measurement based on an electron microscope photograph), and cellulose nanocrystals having a thickness ranging from 10 nm to 50 nm and a length ranging from 100 nm to 500 nm (measurement based on an electron microscope photograph) can also be suitably used as the crystalline cellulose.

I-type crystalline celluloses can be obtained by defibrating cellulose fibers obtained by digesting plant fibers or a commercially available cellulose powder (such as Ceolus (registered trademark) PH1-101 manufactured by Asahi Kasei Corp.) by a mechanical treatment such as a water jet method or by a chemical treatment such as a TEMPO oxidation method. Alternatively, commercially available aqueous dispersion bodies (for example, Ceolus RC manufactured by Asahi Kasei Corp., Rheocrysta (registered trademark) manufactured by DKS Co. Ltd., BiNFi-s (registered trademark) manufactured by Sugino Machine Limited, and Fibnano manufactured by Kusano Sakko Inc.) may be used as I-type crystalline celluloses.

<Production Method of Porous-Cellulose Particles>

Next, a production method of the porous-cellulose particles will be described. First, a dispersion of I-type crystalline cellulose, a surfactant and a nonaqueous solvent are mixed to be emulsified (emulsification step). Then, an emulsified liquid containing an emulsified droplet can be obtained. Next, this emulsified liquid is dehydrated (dehydration step). Then, water in the emulsified droplet is sluggishly removed. Next, a porous-cellulose particle as a solid matter is extracted by solid-liquid separation (solid-liquid separation step). This solid matter is dried and disintegrated to obtain powder of porous-cellulose particles (drying step).

Hereinafter, each step will be described in detail.

[Emulsification Step]

First, a dispersion of I-type crystalline cellulose is prepared. The solid content concentration of this dispersion is adjusted to 0.01 to 5% so that this dispersion has a proper viscosity. When the solid content concentration exceeds 50%, the viscosity usually increases, and the uniformity of the emulsified droplet is sometimes impaired. When the solid content concentration is less than 0.01%, an advantage is not particularly provided, and economy is poor. It is noted that the solvent is preferably water.

This dispersion, a nonaqueous solvent and a surfactant are mixed. The nonaqueous solvent is necessary for emulsification. The nonaqueous solvent may be any common hydrocarbon solvent, as long as it is not compatible with water. The surfactant is added in order to form a water droplet-in-oil type emulsified droplet. A HLB value of the surfactant is preferably in the range of 1 to 10. The HLB value of the surfactant should be optimally selected depending on the polarity of the nonaqueous solvent. The HLB value of the surfactant is particularly preferably in the range of 1 to 5. A combination of surfactants having different HLB values may be used.

Next, this mixed solution is emulsified by an emulsification device. Then, the emulsified condition is set so that an emulsified liquid containing an emulsified droplet of 0.5 to 500 μm can be obtained. In the emulsified droplet, I-type crystalline cellulose dispersed in water exists. As the emulsification device, high-speed shear devices can be adapted. Apart from the emulsification device described above, a high-pressure emulsification device to obtain a finer emulsified droplet, a membrane emulsification device to obtain a more uniform emulsified droplet, and a microchannel emulsification device can be adapted.

It is noted that the average diameter of the emulsified droplets was measured as follows. An emulsified liquid is dropped onto a slide glass and covered by a cover glass. Photographing is performed through the cover glass by a digital microscope (VHX-600 manufactured by Keyence Corporation) at a magnification of 30 to 2000 times to obtain a photograph projection of the emulsified droplets. From this photograph projection, 50 droplets are randomly selected. The circle-equivalent diameters of the droplets are calculated by the attached software. An average value of the 50 circle-equivalent diameters was defined as an average diameter (average droplet diameter).

[Dehydration Step]

Next, the emulsified liquid obtained in the emulsification step is dehydrated. Heating under normal pressure or reduced pressure is performed to vaporize water. This dehydration removes water from the emulsified droplet to obtain a nonaqueous solvent dispersion body containing a porous-cellulose particle having a particle diameter of 0.5 to 25 μm. The porous-cellulose particle is an aggregate of the I-type crystalline cellulose.

Specifically, in a thermal dehydration method under normal pressure, a separable flask equipped with a cooling pipe is heated to perform dehydration while recovering the nonaqueous solvent. Also, in a thermal dehydration method under reduced pressure, heating under reduced pressure is performed using a rotary evaporator or an evaporation can to perform dehydration while recovering the nonaqueous solvent. In the later-described solid-liquid separation step, dehydration is preferably performed until a solid matter of porous-cellulose particles can be extracted from the nonaqueous solvent dispersion body. Since the form as a spherical particle cannot be retained in the solid-liquid separation step if dehydration is insufficient, a high sphericity of the porous-cellulose particles cannot be achieved.

[Solid-Liquid Separation Step]

In the solid-liquid separation step, a solid content is isolated from the nonaqueous solvent dispersion body obtained in the dehydration step by a known method such as filtration or centrifugation. Accordingly, a cake-like substance of the porous-cellulose particle can be obtained.

Furthermore, the cake-like substance obtained in the solid-liquid separation step may be washed to reduce the surfactant. When this porous-cellulose particle is used for liquid formulations such as emulsified products, long-term stability is sometimes impaired by the surfactant. Therefore, it is preferable that the amount of the surfactant remaining in the porous-cellulose particle is 500 ppm or less. For reducing the surfactant, washing with an organic solvent may be performed.

[Drying Step]

In the drying step, heating under normal pressure or reduced pressure is performed to evaporate the nonaqueous solvent from the cake-like substance obtained in the solid-liquid separation step. Accordingly, there is obtained a dried powder of the porous-cellulose particle having an average particle diameter of 0.5 to 25 µm.

Alternatively, the dehydration step may be performed after the emulsified liquid obtained in the emulsification step has been cooled to a range of −50 to 0° C. That is, water in the emulsified droplets is frozen to obtain a frozen emulsion. After the frozen emulsion has been returned to normal temperature, the dehydration step is performed. When the freezing temperature is −50° C. to −10° C., porous-cellulose particles having a solid structure is obtained. When it is −10 to 0° C., porous-cellulose particles having a hollow structure is obtained. At a temperature of about −10 to 0° C., ice crystals gradually grow. As the crystals grow, crystalline celluloses (primary particles) in the droplets are excluded to the outer circumferences of the droplets. Therefore, a cavity is formed inside a shell.

<Cosmetic Product>

Cosmetic products can be prepared by formulating the above-described porous-cellulose particles and various cosmetic ingredients. According to such cosmetic products, there can be simultaneously obtained a rolling feel, persistence of a rolling feel, and uniform spreadability similar to those of inorganic particles (silica particles) containing a single component and soft feel, and moist feel similar to those of plastic beads. That is, representative texture properties required of a texture improver for cosmetic products can be satisfied.

Specifically, cosmetics are shown in Table 1 according to classifications. Such cosmetics can be manufactured by methods known in the art. The cosmetics are used in various forms such as powders, cakes, pencils, sticks, creams, gels, mousse, liquids, and creams.

Representative categories and components of various cosmetic ingredients are illustrated in Table 2. Furthermore, there may be blended cosmetic ingredients described in the Japanese Standards of Quasi-drug Ingredients 2006 (issued by Yakuji Nippo, Limited, Jun. 16, 2006), International Cosmetic Ingredient Dictionary and Handbook (issued by The Cosmetic, Toiletry, and Fragrance Association, Eleventh Edition, 2006), and the like.

TABLE 1

| | |
|---|---|
| Washing cosmetics | Soaps. Cleansing foams. Make-up remover creams. |
| Skincare cosmetics | Moisture retention and skin roughness prevention. Acne. Cuticle care. Massaging. Wrinkle and sag treatments. Dullness and shadow treatments. UV care. Whitening. Antioxidation care. |
| Base makeup cosmetics | Powder foundations. Liquid foundations. Cream foundations. Mousse foundations. Pressed powders. Makeup bases. |
| point makeup cosmetics | Eyeshadows. Eyebrow makeup. Eyeliners. Mascaras. Lipsticks. |
| Hair-care cosmetics | Hair growth. Dandruff prevention. Itch prevention. Conditioning/hair styling. Washing. Perming or waving. Hair coloring or bleaching. |
| Body-care cosmetics | Washing. Sunscreening Hand roughness prevention. Slimming. Blood circulation improvement. Itch suppression. Deodorization. Sweat control. Body hair care. Repellents. Body powders. |
| Fragrance cosmetics | Perfume. Eau de parfum. Eau de toilette. Eau de cologne. Shower cologne. Solid perfume. Body lotion. Bath oil. |
| Oral care products | Toothpastes. Mouthwashes. |

TABLE 2

| Ingredients | Illustration |
|---|---|
| Oils and fats | Olive oil. Rapeseed oil. Beef tallow. Jojoba oil. |
| Waxes | Carnuba wax. Candelilla wax. Beeswax. |
| Hydrocarbons | Paraffin. Squalane. Synthetic and vegetable squalane, α-olefin oligomers. Microcrystalline wax. Pentane. Hexane. |
| Fatty acids | Stearic acid. Myristic acid. Oleic acid. α-hydroxy acid. |
| Alcohols | Isostearyl alcohol. Octyklodecanol. Lauryl alcohol. Ethanol. Isopropanol. Butyl alcohol. Myristyl alcohol. Cetanol. Stearyl alcohol. Behenyl alcohol. |
| Polyhydric alcohols | Ethylne glycol. Triethylene glycol. Polyethylene glycol. Propylene glycol. Glycerin. Diglycerin. 1, 3-butylene glycol. |
| Esters | Alkyl glyceryl ethers. Isopropyl myristate. Isopropyl palmitate. Ethyl stearate. Ethyl oleate. Cetyl laurate. Decyl oleate. |
| Saccharides | Sorbitol. Glucose. Sucrose. Trehalose. Isomerized sugar combination. Pullulan. |
| Silicone oil | Methyl polysiloxane. Methyl hydrogen polysiloxane. Methyl phenyl silicone oil. Various modified silicone oils. Cycle dimethyl silicon oil. |
| Silicone gel | Silicone gel crosslinked by silicone-based and/or other organic compounds. |
| Surfactants | Nonionic. Cationic. Anionic surfactants. |
| Fluorine oil | Perfluoropolyether |
| Various polymers | Gum arabic. Carrageenan. Agar. Xanthan gum. Gelatin. Alginic acid. Pllulan. Albumin. Guar gum. Polyvinyl alcohol. Cellulose and derivatives thereof. Carboxyvinyl polymers. Polyacrylic acid amide. Sodium polyacrylate. |
| UV protectors | Cinnamic acid such as octyl paramethoxycinnamate. Salicylic acid. Benzoic acid ester. Urocanic acid. Benzophenone. |
| Inorganic compounds | Titanium oxide. Zinc oxide. Aluminum oxide. Aluminum hydroxide. Red iron oxide. Yellow iron oxide. Black iron oxide. Cerium oxide. Zirconium oxide. Silica. Mica. Talc. Sericite. Boron nitride. Barium sulfate. Mica titanium having peal-like gloss. Composites |

TABLE 2-continued

| Ingredients | Illustration |
| --- | --- |
| | thereof. (Here, the surface of inorganic compounds such as titanium oxide and zinc oxide may be previously subjected to a silicone treatment, a fluorine treatment, a metal soap treatment, or the like.) |
| Resin particles | Methyl polyacrylate. Nylon. Silicone resin. Silicone rubber. Polyethylene. Polyester. Polyurethane. |
| Ingredients having whitening effects | Arbutin. Kojic acid. Vitamin C. Lanolic acid. Linoleic acid. Lactic acid. Tranexamic acid. Ascorbic acid derivatives (sodium ascorbate, magnesium ascorbate phosphate, ascorbyl dipalmitate, glucoside ascorbate, others). Plant extracts (placenta extracts, sulfur, oil-soluble licorice extracts, mulberry extracts). |
| Ingredients having rough skin remedying effects | Various vitamins. Carotinoid. Flavonoid. Tannin. Caffeic acid derivatives. Lignan. Saponin. Amino acid. Betaine. Ceramide. Sphingolipid. Retinoic acid and retinoic acid structural analogs. N-acetylglucosamine. ε-aminocaproic acid. α-hydroxy acid. Glycyrrhizic acid. Biopolymers (sodium hyaluronate, collagen, elastin, chitin/chitosan, sodium chondroitin sulphateamino acid). Cholesterol and derivatives thereof. |
| Other ingredients | Antiseptic and preservative agents. Antioxidants. Solvents. Flavors. Water. Modified or unmodified clay minerals. Various organic pigments and dyes. |

EXAMPLES

Hereinafter, examples of the present invention will be specifically described.

Example 1

First, a dispersion liquid of I-type crystalline celluloses is prepared. In the present example, 50 g of type I celluloses (Ceolus PH-101 manufactured by Asahi Kasei Corp.) was suspended in 4950 g of pure water. This suspension liquid passed through a Microfluidizer (M-7250-30 manufactured by Microfluidics Co.) 100 times, thereby to prepare a dispersion liquid having a solid content concentration of 1%.

This dispersion liquid, a water-insoluble solvent, and a surfactant are mixed. In the present example, 50 g of the dispersion liquid was diluted with 150 g of pure water to have a solid content concentration of 0.25%. This diluted dispersion liquid was added into a mixed solution of 3346 g of heptane (manufactured by Kanto Chemical Co., Inc.) and 25 g of an AO-10 V surfactant (manufactured by Kao Corporation). The mixture was stirred using an emulsification disperser (T.K. ROBOMIX manufactured by PRIMIX Corporation) at 10000 rpm for 10 minutes. This initiated emulsification, and an emulsified liquid containing emulsified droplets was obtained. This emulsified liquid was heated at 60° C. for 16 hours to dehydrate the emulsified droplets. Furthermore, a Buchner funnel (3.2 L, manufactured by Sekiya Chemical Glass Apparatus Co., Ltd.) was used to perform filtration through a quantitative filter paper (No. 2, manufactured by Advantec Toyo Kaisha, Ltd.). Thereafter, washing with heptane was repeated to remove the surfactant. The thus obtained cake-like substance was dried at 60° C. for 12 hours. This dried powder passed through a 250-mesh sieve (standard sieve for JIS test), and a powder of the porous-cellulose particles was obtained. A SEM photograph of the porous-cellulose particles is illustrated in FIG. 1.

The preparation conditions of the porous-cellulose particles are illustrated in Table 3. Also, physical properties of the powder of the porous-cellulose particles were measured in the following method. The results are illustrated in Table 4.

(1) Average Particle Diameter ($d_1$, $d_3$) and Coefficient of Particle Variance (CV) of Particles The particle size distribution of particles was measured by laser diffractometry. A median value calculated from this particle size distribution was defined as an average particle diameter. In this manner, the average particle diameter $d_1$ of the porous-cellulose particles and the average particle diameter $d_3$ of the I-type crystalline celluloses were calculated. Furthermore, from the particle size distribution (population) of the porous-cellulose particles, a standard deviation σ and a population mean μ were calculated to further obtain the coefficient of particle variance (CV=σ/μ) of the porous-cellulose particles. In Table 4, these are indicated in percentage. As described herein, the particle size distribution was measured using an LA-950v2 laser diffraction/scattering particle diameter distribution measuring apparatus (manufactured by Horiba, Ltd.). However, for the average particle diameter $d_1$ of the fibrous I-type crystalline celluloses represented by cellulose nanofibers and cellulose nanocrystals, an average particle diameter in terms of an equivalent sphere was calculated according to the formula "average particle diameter=6000/(true density×specific surface area)".

(2) Average Particle Diameter Ratio Between with and without Ultrasonic Dispersion Dispersion was performed using a laser diffraction/scattering particle diameter distribution measuring apparatus (LA-950v2) by setting the dispersion conditions to "ultrasonic for 60 minutes". After this ultrasonic dispersion test, a particle size distribution of the porous-cellulose particles was measured. A median value in this particle size distribution was defined as an average particle diameter da after the ultrasonic dispersion. Based on this, an average particle diameter ratio ($d_2/d_1$) before and after the ultrasonic dispersion test was calculated.

(3) A Sphericity of the Porous-Cellulose Particles

A photograph projection was obtained by photographing the particles with a magnification of 2,000 to 250,000 using a transmission electron microscope (H-8000, manufactured by Hitachi, Ltd.), and arbitrary 50 particles were selected from the photograph projection. For each of the selected particles, the maximum diameter (DL) and the short diameter (DS) orthogonal to the maximum diameter (DL) were measured, and the ratio (DS/DL) was obtained. The mean value of the ratios was determined as the sphericity.

(4) A Specific Surface Area of the Porous-Cellulose Particles

About 30 ml of the porous-cellulose particle powder was put in a porcelain crucible (type B-2) and dried at 105° C. for two hours. Thereafter, the porous-cellulose particle powder was cooled to room temperature in a desiccator. Next, 1 g of the sample was taken and the specific surface area ($m^2/g$) thereof was measured by the BET method using a full-automatic surface area measuring device (Multisorb 12, manufactured by Yuasa Ionics Inc.). The specific surface area per unit volume was obtained by converting the measured specific surface area with the specific gravity of I-type crystalline cellulose (1.5 g/cm$^3$) formulated in the porous-cellulose particle.

(5) Pore Volume and Pore Diameter of Porous-Cellulose Particles

Ten grans of the powder of the porous-cellulose particles was sampled into a crucible and dried at 105° C. for 1 hour. Thereafter, the resultant product was poured in a desiccator and cooled to room temperature. Next, 0.15 g of the sample was poured in a washed cell. While vacuum deaeration is performed using a Belsorp mini II (manufactured by Bell Japan. Inc.), nitrogen gas is adsorbed to this sample. Thereafter, nitrogen is desorbed. From the obtained adsorption isotherm, an average pore diameter is calculated by a BJH method. Also, from the formula "pore volume (ml/g)= (0.001567×(V−Vc)/W)", a pore volume was calculated. Here, V represents an adsorption amount (ml) in a standard state at a pressure of 735 mnHg. Vc represents a volume (ml) of a cell blank at a pressure of 735 mmHg. W represents a mass (g) of the sample. Also, a density ratio between nitrogen gas and liquid nitrogen was defined as 0.001567.

Example 2

Two hundred grams of the dispersion liquid having a solid content concentration of 1% obtained in Example 1 was added into a mixed solution of 3346 g of heptane and 25 g of a surfactant (AO-10 V). This liquid was stirred using an emulsification disperser at 10000 rpm for 10 minutes for emulsification. The thus obtained emulsified liquid was left to stand in a constant temperature bath at −5° C. for 72 hours to freeze water in the emulsified droplets. Thereafter, this liquid was increased to normal temperature for thawing. The thawed product was filtered through a quantitative filter paper using a Buchner funnel. Furthermore, washing with heptane was repeated to remove the surfactant. From the thus obtained cake-like substance, a powder of the porous-cellulose particles was obtained in the same manner as Example 1. Physical properties of this powder were measured in the same manner as Example 1.

The internal structure of the porous-cellulose particles obtained in the present example was studied. To about 1 g of epoxy resin (EPO-KWICK manufactured by BUEHLHER), 0.1 g of the powder was uniformly mixed. The mixture was hardened at normal temperature. Thereafter, a sample was prepared using a FIB processor (manufactured by Hitachi, Ltd., FB-2100). A SEM image of this sample was photographed using a transmission electron microscope (manufactured by Hitachi, Ltd., HF-2200) under the condition of an acceleration voltage of 200 kV. As a result, this sample was particles having a hollow structure in which a cavity was formed inside a shell. From this SEM image, a thickness T of the shell and an outer diameter OD were measured, and a thickness ratio (T/OD) of the shell was calculated.

Example 31

An emulsified liquid was prepared in the same manner as Example 2. This emulsified liquid was left to stand in a freezer at −25° C. for 72 hours. Thereafter, porous-cellulose particles were prepared, and physical properties of the prepared particles were measured, in the same manner as Example 2.

Example 4

A dispersion liquid having a solid content concentration of 1% was prepared using a BiNFi-s WMa-10002 (manufactured by Sugino Machine Limited) as type I celluloses instead of a Ceolus PH-101 of Example 1. Two hundred grams of this dispersion liquid was added into a mixed solution of 3346 g of heptane and 25 g of a surfactant (AO-10 V). Thereafter, porous-cellulose particles were prepared, and physical properties of the prepared particles were measured, in the same manner as Example 1.

Example 51

A dispersion liquid having a solid content concentration of 1% was prepared in the same manner as Example 1. Two hundred grams of this dispersion liquid was added into a mixed solution of 3346 g of heptane and 25 g of a surfactant (AO-10 V). Thereafter, porous-cellulose particles were prepared, and physical properties of the prepared particles were measured, in the same manner as Example 1. However, the rotation speed of the emulsification disperser during emulsification was changed to 2000 rpm, and the heating time (dehydration time) of the emulsified liquid was changed to 24 hours.

Example 6

The rotation speed of the emulsification disperser during emulsification was changed to 5000 rpm, and the heating time of the emulsified liquid was changed to 16 hours. Otherwise, porous-cellulose particles were prepared, and physical properties of the prepared particles were measured, in the same manner as Example 5.

Example 7

A dispersion liquid having a solid content concentration of 1% was prepared using an 1-2SP manufactured by DKS Co. Ltd. as type I celluloses. Otherwise, porous-cellulose particles were prepared, and physical properties of the prepared particles were measured, in the same manner as Example 4.

Example 8

The rotation speed of the emulsification disperser during emulsification was changed to 800 rpm. Otherwise, porous-cellulose particles were prepared, and physical properties of the prepared particles were measured, in the same manner as Example 5.

Comparative Example 1

Porous-cellulose particles were prepared, and physical properties of the prepared particles were measured, in the same manner as Example 4 except that the dehydration condition of the emulsified liquid was changed to 40° C. for 4 hours.

Comparative Example 2

In the present comparative example, particles of gathered crystalline celluloses were prepared by a spray drying method without using an emulsification method. Twenty grams of a Ceolus PH-101 manufactured by Asahi Kasei Corp., 75 g of urea, 23 g of lithium hydroxide, and 500 g of distilled water were mixed. This mixed liquid was cooled in a constant temperature bath at −25° C. for 2 hours. The temperature of the resultant product was increased to normal temperature for thawing. Accordingly, a solution in which celluloses are dissolved is obtained. With this solution as a spray liquid, spray drying was performed by a spray dryer (manufactured by NIRO Co., NIRO-ATMIZER). That is, spray drying was performed by supplying the spray liquid at a flow rate of 2 L/hr from one of two fluid nozzles and gas at a pressure of 0.15 MPa from the other into a dry gas stream set at an inlet temperature of 150° C. and an outlet temperature of 50 to 55° C. The thus obtained dried powder is celluloses having a type II crystal form. The powder was suspended in pure water and filtered through a quantitative filter paper (No. 2, manufactured by Advantec Toyo Kaisha, Ltd.) using a Buchner funnel (3.2 L, manufactured by Sekiya Chemical Glass Apparatus Co., Ltd.). Thereafter, washing with pure water is repeated to obtain a cake-like substance. This cake-like substance was dried at 120° C. for 16 hours and thereafter passed through a 250-mesh sieve (standard sieve for JIS test), thereby to obtain a powder of porous-cellulose particles. Physical properties of this powder were measured in the same manner as Example 1.

Comparative Example 3

In the present comparative example, a 4% dispersion liquid was used instead of a dispersion liquid having a solid content concentration of 1% in Example 5. That is, 200 g of type I celluloses (Ceolus PH-101 manufactured by Asahi Kasei Corp.) was suspended in 4800 g of pure water, thereby to prepare a dispersion liquid having a solid content concentration of 4%. Otherwise, porous-cellulose particles were prepared, and physical properties of the prepared particles were measured, in the same manner as Example 5. However, the rotation speed of the emulsification disperser in the emulsification step was set at 800 rpm.

Comparative Example 4

Figure 2:
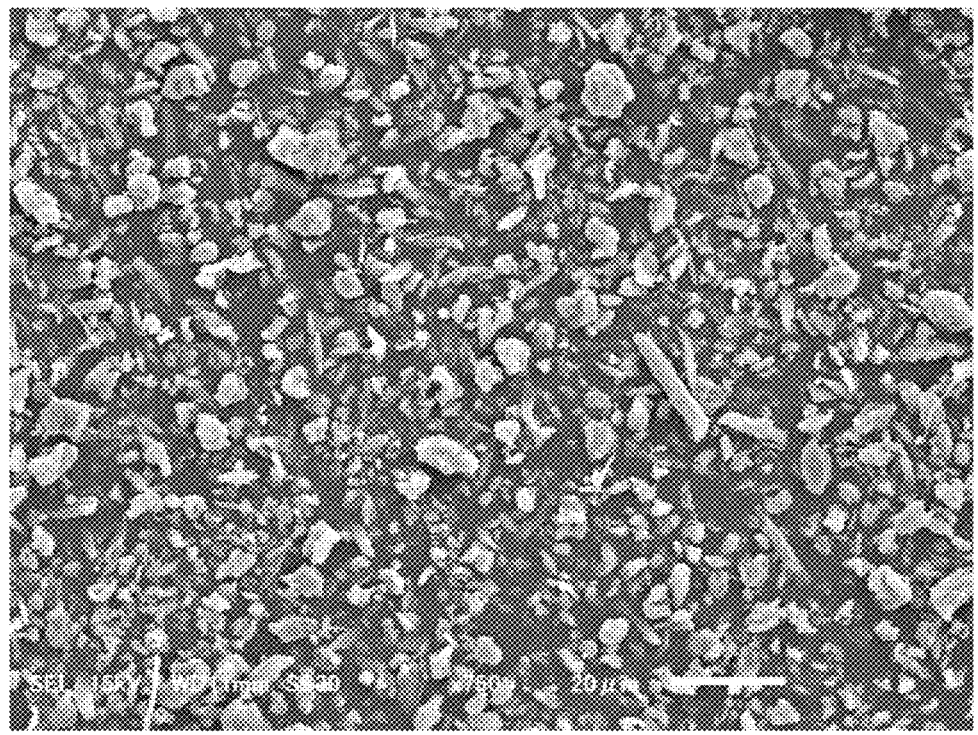
FIG. 2 is a SEM photograph illustrating appearances of porous-cellulose particles according to Comparative Example 4.

In the present comparative example, particles of gathered crystalline celluloses were prepared by a spray drying method without using an emulsification method. Cut dissolving pulp (DP) was added in a 7% aqueous HCl solution. The resultant product was heated at 105° C. for 20 minutes, thereby to perform hydrolysis. An acid-insoluble residue which had not dissolved was subjected to neutralization, washing, and filtration and dehydration, thereby to obtain a wet cake (water content 50%). Using a kneader (10 L), 3.0 kg of this wet cake was kneaded and ground for about 1 hour. The moisture contained in the obtained cake was replaced with isopropyl alcohol (hereinafter, IPA), thereby to prepare a slurry having a solid content concentration (solid component: cellulose) of 5.5% and containing 0.4% of moisture and 94.1% of IPA. This slurry was observed through an electron microscope. As a result, the most of the observable particles were 1 μm or less. This slurry was spray dried using a spray dryer (nitrogen circulation type (explosion proof specification)). The obtained dried powder passed through a 330-mesh sieve (standard sieve for JIS test), thereby to obtain a powder of porous-cellulose particles. A SEM photograph of the porous-cellulose particles is illustrated in FIG. 2. According to this SEM photograph, particles having a shape close to a sphere and particles having an indefinite shape such as fibrous or rod-like shape co-exist, which indicates that variations in sphericity of particles are large. Physical properties of the porous-cellulose particles were measured in the same manner as Example 1.

TABLE 3

| | crystalline cellulose dispersion liquid | | Emulsification condition | | Emulsification (or frozen) condition | |
|---|---|---|---|---|---|---|
| | | Average particle | | Emulsification | | |
| | Type | diameter ($d_3$) [nm] | concentration [%] | dispersion rate [rpm] | Emulsification time (min.) | Condition | Time [Hr.] |
| Example 1 | ① | 300 | 0.25 | 10000 | 10 | Heating (60° C.) | 16 |
| Example 2 | ① | 300 | 1.0 | 10000 | 10 | Freezing (−5° C.) | 72 |
| Example 3 | ① | 300 | 1.0 | 10000 | 10 | Freezing (−25° C.) | 72 |
| Example 4 | ② | 100 | 1.0 | 10000 | 10 | Heating (60° C.) | 16 |
| Example 5 | ① | 300 | 1.0 | 2000 | 10 | Heating (60° C.) | 24 |
| Example 6 | ① | 300 | 1.0 | 5000 | 10 | Heating (60° C.) | 16 |
| Example 7 | ③ | 9 | 1.0 | 10000 | 10 | Heating (60° C.) | 16 |
| Example 8 | ① | 300 | 1.0 | 800 | 10 | Heating (60° C.) | 24 |
| Comparative Example 1 | ② | 100 | 1.0 | 10000 | 10 | Heating (60° C.) | 4 |
| Comparative Example 2 | ① | 300 | 1.0 | — | — | — | — |
| Comparative Example 3 | ① | 300 | 4.0 | 800 | 10 | Heating (60° C.) | 24 |
| Comparative Example 4 | — | 400 | 5.5 | — | — | — | — |

①: Ceolus (registered trademark) PH-101 manufactured by Asahi Kasei Corporation (I-type crystalline cellulose)
②: BiNFi-s WMa-10002 manufactured by Sugino Machine Limited (I-type crystalline cellulose)
③: I-2SP manufactured by DKS Co. Ltd. (I-type crystalline cellulose)

TABLE 4

| | Porous cellose particle | | | | | | | | |
|---|---|---|---|---|---|---|---|---|---|
| | Average particle diameter ($d_1$) μm | Specific surface area m²/g | Sphericity | CV % | Pore volume ml/g | average pore diameter nm | $d_2/d_1$ | Interior structure | T/OD |
| Example 1 | 1.2 | 40 | 0.95 | 12 | 0.2 | 40 | 1.01 | Porous solid | — |
| Example 2 | 4.3 | 39 | 0.90 | 20 | 0.9 | 40 | 1.01 | Nonporous hollow | 0.11 |
| Example 3 | 4.8 | 55 | 0.88 | 20 | 0.9 | 66 | 1.01 | Porous solid | — |
| Example 4 | 5.0 | 120 | 0.87 | 26 | 0.3 | 40 | 1.01 | Porous solid | — |
| Example 5 | 13.2 | 40 | 0.88 | 33 | 0.2 | 40 | 1.01 | Porous solid | — |
| Example 6 | 9.3 | 40 | 0.89 | 28 | 0.2 | 40 | 1.01 | Porous solid | — |
| Example 7 | 4.4 | 450 | 0.92 | 24 | 0.3 | 22 | 1.00 | Porous solid | — |
| Example 8 | 39.3 | 40 | 0.86 | 38 | 0.2 | 40 | 1.01 | Porous solid | — |
| Comparative Example 1 | 5.1 | 119 | 0.52 | 52 | 1 | 41 | 0.96 | Porous solid | — |
| Comparative Example 2 | 3.8 | 2 | 0.91 | 32 | 0.04 | — | 1.04 | Porous solid | — |
| Comparative Example 3 | 83.0 | 41 | 0.85 | 51 | 0.2 | 40 | 1.02 | Porous solid | — |
| Comparative Example 4 | 5.0 | 140 | 0.55 | 182 | 0.6 | 55 | 0.82 | Porous solid | — |

[Texture Properties of Power of Porous-Cellulose Particle]

Next, the powders obtained in Examples and Comparative Examples were evaluated for their texture properties. Each of the powders was subjected to a sensory test by 20 expert panelists. The panelists are interviewed regarding seven evaluation items: smooth and dry feel, moist feel, rolling feel, uniform spreadability, adhesiveness to skin, persistence of rolling feel, and soft feel. Evaluation is performed in accordance with the following evaluation point criteria (a). Based on the total of the evaluation points by the panelists, the texture of the porous-cellulose particle was evaluated in accordance with the following evaluation criteria (b). The results are illustrated in Table 5. As a result, it was found that the powders of Examples are significantly excellent as a texture improver for cosmetic products, but the powders of Comparative Examples are not suitable as a texture improver.

Evaluation Point Criteria (a)
  5 points: Very superior
  4 points: Superior
  3 points: Average
  2 points: Inferior
  1 point: Very inferior Evaluation Criteria (b)
  Excellent: 80 points or more in total
  Good: 60 points or more and less than 80 points in total
  Fair: 40 points or more and less than 60 points in total
  Poor: 20 points or more and less than 40 points in total
  Bad: less than 20 points in total

TABLE 5

| Evaluation sample | Smooth and dry feel | Moist feel | Rolling feel | Uniform spreadability | Adhesiveness to skin | Persistence of rolling feel | Soft feel |
|---|---|---|---|---|---|---|---|
| Example 1 | Good | Good | Good | Good | Excellent | Good | Good |
| Example 2 | Good | Excellent | Good | Good | Good | Good | Excellent |
| Example 3 | Excellent | Fair | Good | Fair | Poor | Good | Good |
| Example 4 | Good | Good | Excellent | Good | Good | Excellent | Good |
| Example 5 | Excellent | Poor | Excellent | Fair | Poor | Excellent | Poor |
| Example 6 | Excellent | Fair | Excellent | Fair | Fair | Excellent | Fair |
| Example 7 | Good | Excellent | Good | Good | Good | Excellent | Good |
| Example 8 | Excellent | Bad | Excellent | Poor | Bad | Excellent | Poor |
| Comparative Example 1 | Good | Fair | Bad | Bad | Poor | Bad | Poor |
| Comparative Example 2 | Bad | Excellent | Good | Poor | Excellent | Good | Good |
| Comparative Example 3 | Excellent | Bad | Excellent | Bad | Bad | Excellent | Bad |
| Comparative Example 4 | Bad | Fair | Poor | Bad | Good | Bad | Bad |

[Feeling of Using Powder Foundation]

Using the porous-cellulose particles powder, powder foundation was formed at the blend ratios % by weight) illustrated in Table 6. The powder of particles of each Example (ingredients (1)) and other ingredients (2) to (9) were poured into a mixer. The mixture was stirred to be uniformly mixed. Next, cosmetic ingredients (10) to (12) were poured into this mixer. The mixture was stirred to be further uniformly mixed. The obtained cake-like substance was disintegrated. Thereafter, about 12 g of the disintegrated substance was taken, and placed in a 46 mm×54 mm×4 mm square metal dish for press molding. Twenty specialized panelists conducted a sensory test on this obtained powder foundation. In the test, the following six evaluation items were studied by hearing: uniform spreadability, moist feel, and smoothness during application onto the skin, and uniformity of film, moist feel, and softness after application to the skin. The results are evaluated based on the above-described evaluation point criteria (a). Also, evaluation points scored by the panelists were totaled, and the use feels of the foundation was evaluated based on the above-described evaluation criteria (b). The results are illustrated in Table 7. Here, cosmetic products A to H according to Examples were evaluated as representative examples. It was found that the feeling of using the cosmetic products A to H based on Examples is very superior both during and after the application. However, it was found that the feeling of using cosmetic products a to d of Comparative Examples is not good.

TABLE 6

| | Cosmetic ingredients constituting powder foundation | Blend amount: [weight (%)] |
|---|---|---|
| (1) | Powder according to Example or Comparative Example | 10.0 |
| (2) | Sericite (silicon treatment) | 40.0 |
| (3) | Talc (silicon treatment) | 29.0 |
| (4) | Mica (silicon treatment) | 5.0 |
| (5) | Titanium oxide (silicon treatment) | 7.0 |
| (6) | Yellow iron oxide (silicon treatment) | 1.2 |
| (7) | Red iron oxide (silicon treatment) | 0.4 |
| (8) | Black iron oxide (silicon treatment) | 0.2 |
| (9) | Methyl paraben | 0.2 |
| (10) | Dimethicone | 4.0 |
| (11) | Liquid paraffin | 2.0 |
| (12) | Glyceryl tri 2-ethylhxanoate | 1.0 |

TABLE 7

| | During application | | | After application | | |
|---|---|---|---|---|---|---|
| Evaluation sample | Uniform spreadability | Moist feel | Smoothness | Uniformity of film | Moist feel | Softness |
| Example 1 (Cosmetic A) | Good | Excellent | Good | Good | Excellent | Good |
| Example 2 (Cosmetic B) | Good | Excellent | Excellent | Excellent | Excellent | Excellent |
| Example 3 (Cosmetic C) | Good | Good | Good | Good | Good | Good |
| Example 4 (Cosmetic D) | Excellent | Good | Excellent | Good | Good | Good |
| Example 5 (Cosmetic E) | Good | Fair | Fair | Good | Fair | Good |
| Example 6 (Cosmetic F) | Good | Good | Good | Good | Good | Good |
| Example 7 (Cosmetic G) | Excellent | Good | Excellent | Good | Excellent | Excellent |
| Example 8 (Cosmetic H) | Fair | Fair | Fair | Fair | Fair | Fair |
| Comparative Example 1 (Cosmetic a) | Bad | Fair | Bad | Bad | Fair | Bad |
| Comparative Example 2 (Cosmetic b) | Bad | Good | Good | Bad | Good | Good |
| Comparative Example 3 (Cosmetic c) | Bad | Poor | Bad | Bad | Poor | Poor |
| Comparative Example 4 (Cosmetic d) | Bad | Poor | Bad | Bad | Poor | Bad |

The invention claimed is:

1. Porous-cellulose particles, each porous-cellulose particle comprising crystalline celluloses having a type I crystal form, wherein
   the crystalline celluloses includes a glucose molecule as a constitutional unit, and
   the porous-cellulose particles have an average particle diameter $d_1$ of 0.5 μm to less than 50 μm, a specific surface area of 25 m²/g to 1000 m²/g, and a sphericity of 0.85 or more.

2. The porous-celluloses particles according to claim 1, which have a coefficient of particle variance (CV) of 50% or less.

3. The porous-cellulose particles according to claim 1, which have a pore volume (PV) of 0.2 ml/g to 5.0 ml/g.

4. The porous-cellulose particles according to claim 3, which have an average pore diameter (PD) of 2 nm to 200 nm.

5. The porous-cellulose particles according to claim 1, wherein a ratio ($d_2/d_1$) is in a range of 0.95 to 1.05, the $d_2$ is an average particle diameter of the porous-cellulose particles when an aqueous dispersion liquid of the porous-cellulose particles is dispersed by an ultrasonic disperser for 60 minutes.

6. The porous-cellulose particles according to claim 1, wherein an average particle diameter $d_3$ of the crystalline celluloses is from 1 nm to 1 µm.

7. The porous-cellulose particles according to claim 1, wherein the porous-cellulose particles are hollow particles having a cavity inside a shell.

8. A production method of the porous-cellulose particles according to claim 1, comprising:
   an emulsification step of mixing a dispersion liquid of crystalline celluloses having a type I crystal form, a surfactant, and a nonaqueous solvent to prepare an emulsified liquid containing emulsified droplets;
   a dehydration step of removing water from the emulsified droplets; and
   a step of separating the nonaqueous solvent dispersion body obtained in the dehydration step into solid and liquid to obtain porous-cellulose particles as solid matter.

9. The production method of porous-cellulose particles according to claim 8, wherein the dehydration step is performed after cooling the emulsified liquid obtained in the emulsification step to a range of 0° C. to −50° C. to obtain a frozen emulsified liquid in which water in the emulsified droplets is frozen and then returning the frozen emulsified liquid to normal temperature.

10. Cosmetic products containing the porous-cellulose particles according to claim 1.

* * * * *